| United States Patent [19] | [11] Patent Number: 4,582,923 |
|---|---|
| Stammann et al. | [45] Date of Patent: Apr. 15, 1986 |

[54] PROCESS FOR THE PRODUCTION OF URETHANES

[75] Inventors: Günter Stammann, Cologne; Robert Becker, Leverkusen; Johann Grolig, Leverkusen; Helmut Waldmann, Leverkusen, all of Fed. Rep. of Germany

[73] Assignee: Bayer Aktiengesellschaft, Leverkusen, Fed. Rep. of Germany

[21] Appl. No.: 735,249

[22] Filed: May 17, 1985

Related U.S. Application Data

[63] Continuation of Ser. No. 328,153, Dec. 7, 1981.

[30] Foreign Application Priority Data

Dec. 12, 1980 [DE] Fed. Rep. of Germany ....... 3046982

[51] Int. Cl.$^4$ .............. C07C 125/067; C07C 125/065; C07C 125/073; C07C 125/075
[52] U.S. Cl. ...................................... 560/24; 560/25; 560/29; 560/30; 560/22; 560/13; 560/115; 560/157; 560/158; 560/162; 560/163; 546/159; 546/309; 548/163; 548/558; 548/557; 549/480; 549/69
[58] Field of Search ............ 560/24, 25, 32, 163, 560/157, 162, 158, 115, 30, 29, 22, 13; 546/309, 159; 548/557, 558, 163; 549/480, 69; 260/465.4

[56] References Cited

U.S. PATENT DOCUMENTS

| 3,641,092 | 2/1972 | Henry | 560/157 X |
|---|---|---|---|
| 4,236,016 | 11/1980 | Scholl et al. | 560/24 |
| 4,251,667 | 2/1981 | Kesling, Jr. | 560/24 |
| 4,260,781 | 4/1981 | Harvey | 560/157 X |
| 4,266,070 | 5/1979 | Moy | 560/24 |
| 4,267,353 | 5/1981 | Scholl et al. | 560/24 |
| 4,297,501 | 10/1981 | Becker et al. | 560/24 |
| 4,319,035 | 3/1982 | Merger et al. | 560/24 X |

FOREIGN PATENT DOCUMENTS

2910132 9/1980 Fed. Rep. of Germany .

*Primary Examiner*—Bernard Helfin
*Attorney, Agent, or Firm*—Gene Harsh; Joseph C. Gil; Lyndanne M. Whalen

[57] ABSTRACT

Urethanes are made by reacting a primary amine with carbon monoxide and a compound containing at least one hydroxyl group in the presence of an oxidizing agent and a catalyst system. The catalyst system is made up of (i) a noble metal and/or a noble metal compound of a metal of the Eighth Secondary Group of the Periodic System of Elements and (ii) an oxidizing quinoid and/or a compound capable of being converted to an oxidizing quinoid compound under the reaction conditions. The catalyst system may optionally include (iii) metal compounds of elements of the Third to Fifth Main Groups and/or First to Eighth Secondary Groups of the Periodic System of Elements and/or (iv) a tertiary amine. This reaction is generally carried out at a temperature of from 100° to 300° C. and at a pressure of from 5 to 500 bars. The product urethanes are useful in the production of isocyanates and pesticides.

11 Claims, No Drawings

PROCESS FOR THE PRODUCTION OF URETHANES

This application is a continuation of application Ser. No. 328,153 filed Dec. 7, 1981.

BACKGROUND OF THE INVENTION

This invention relates to a process for the production of urethanes (carbamic acid esters or carbamates). More specifically, it relates to a process in which primary amines are reacted with organic hydroxyl compounds and carbon monoxide in the presence of an oxidizing agent and in the presence of a catalyst system. The catalyst system includes at least one noble metal or at least one noble metal compound, and a quinoid compound or compound capable of being converted into a quinoid compound.

Generally, organic isocyanates are commercially produced by reacting the corresponding amine with phosgene. However, due to the high chlorine demand and the high energy costs involved in the production of phosgene, considerable efforts have been exerted to find a commercially workable method for producing organic isocyanates in which there is no need to use phosgene. In one such method, primary amines are reacted with carbon monoxide, organic hydroxyl compounds and an oxidizing agent (such as air or an organic nitro compound) to form the corresponding urethanes; the urethanes thus formed are then split into isocyanates and compounds containing hydroxyl groups. This phosgene-free process for producing urethanes is described in German Offenlegungsschrift No. 2,910,132 and in German Offenlegungsschrift No. 2,908,251 (=EP-OS No. 16346 or U.S. Ser. No. 125,394 filed Feb. 27, 1980). In the process described in German Offenlegungsschrift No. 2,908,251, primary amines are catalytically oxycarbonylated by reaction with carbon monoxide, organic hydroxyl compounds, an oxidizing agent which is either molecular oxygen or a nitro compound and a catalyst. The disclosed catalyst is, from 1 to 5 weight % (based on the mixture as a whole,) of chloride-containing, inorganic solids which are largely insoluble in the reaction mixture used in combination with a noble metal catalyst. This latter process, however, is disadvantageous in that the high content of chloride-containing compounds causes corrosion problems in the process apparatus. Additionally, the fact that the inorganic catalyst components are substantially insoluble seriously affects the commercial practicability of the known process.

SUMMARY OF THE INVENTION

It is an object of the present invention to provide a process for the production of urethanes from primary amines.

It is another object of the present invention to provide a process for the production of urethanes from primary amines which does not require the use of phosgene.

It is also an object of the present invention to provide a process for the production of urethanes from primary amines in which insoluble and/or corrosive catalysts need not be used.

These and other objects which will be apparent to those skilled in the art are accomplished by reacting a primary amine with carbon monoxide and a compound having at least one hydroxyl group in the presence of an oxidizing agent and a catalyst system. A suitable catalyst system includes a noble metal and/or noble metal compound of Group VIII b of the Periodic System of Elements and an oxidizing quinoid compound and/or a compound capable of being converted to an oxidizing quinoid compound under the reaction conditions.

DETAILED DESCRIPTION OF THE INVENTION

The present invention relates to a process for the production of urethanes in which primary amines are reacted with carbon monoxide and compounds containing at least one hydroxyl group in the presence of oxidizing agents and a catalyst system. Appropriate catalyst systems contain at least one noble metal and/or noble metal compound from the Eighth Secondary Group of the Periodic System of Elements, and at least one oxidizing quinoid compound and/or at least one compound which may be converted under the reaction conditions into an oxidizing quinoid compound.

Primary amines which may be used in the practice of the present invention are any organic compounds containing at least one primary amino group, particularly primary amines containing at least one aliphatically, cycloaliphatically, aromatically or heterocyclically bound amino group which amines may optionally contain other functional groups. It is preferred to use aromatic or aliphatic monoamines or diamines, particularly monoamines which do not contain any oxidizable substituents other than the primary amino groups. The amines used in the practice of the present invention generally have a molecular weight in the range from 31 to 3000, preferably in the range from 31 to 400 and most preferably in the range from 31 to 200.

Examples of suitable aromatic and heterocyclic amines include aniline, 1,2-diaminobenzene, 1,4-diaminobenzene, the isomeric chloroanilines, 3,4-dichloroaniline, 4-isopropyl aniline, p-toluidine, chlorotoluidines, xylidines, alkoxy anilines, 4-pentachloroethyl aniline, 2-nitroaniline, 3-nitroaniline, 4-nitroaniline, 2,3-diaminotoluene, 2,4-diaminotoluene, 2,6-diaminotoluene, 2,5-diaminotoluene, 3,4-diaminotoluene, 3,5-diaminotoluene, 2-amino-4-nitrotoluene, 2-amino-3-nitrotoluene, 2-amino-5-nitrotoluene, aminophenols, diaminoxylenes, aminonitroxylenes, aminonaphthalenes, aminoanthracenes, chloroaminobenzoic acids, chloroaminobenzoic acid esters, aminobenzene sulfonic acids, 4,4'-diaminodiphenylmethane, 2,2'-diaminodiphenylmethane, 2,4-diaminodiphenylmethane, tris-(4-aminophenyl)-methane, aminopyridines, aminoquinolines, aminopyrroles, aminofurans, aminothiophenes and 2-aminobenzothiazole.

Examples of suitable cycloaliphatic primary amines are aminocyclobutane, aminocyclopentane, cyclohexylamine, 1,2-diaminocyclohexane, 1,3-diaminocyclohexane, 1,4-diaminocyclohexane, bis-(aminocyclohexyl)-methanes and tris-(aminocyclohexyl)-methanes.

Examples of appropriate aliphatic primary amines include: methylamine, ethylamine, 1-propylamine, 2-propylamine, 1-butylamine, 2-butylamine, isobutylamine, tert.-butylamine, 1-pentylamine, 1-hexylamine, 1-heptylamine, 1-octylamine, 1-decylamine, 1-dodecylamine, ethylene diamine, 1,2-diamino-propane, 1,3-diaminopropane, diaminobutanes, diaminopentanes, diaminohexanes, diaminooctanes, diaminodecanes, benzylamine, bis-(aminomethyl)-cyclohexanes, bis-(aminomethyl)-benzene, ω-aminocarboxylic acid esters, and ω-aminocarboxylic acid nitriles.

Particularly preferred primary amines are aromatic primary amines, such as aniline, substituted anilines, the isomeric diaminotoluenes and 4,4'-diaminodiphenyl methane.

Organic compounds containing hydroxyl groups which may be used in the practice of the present invention are any organic compounds which contain at least one alcoholically or phenolically bound hydroxyl group and which have a molecular weight in the range from 32 to 2000 (preferably in the range from 32 to 300). Alcohols are the preferred hydroxy materials.

Suitable alcohols include: any linear or branched monohydric or polyhydric alkanols or alkenols, any monohydric or polyhydric cycloalkanols, cycloalkenols and aralkanols. Any alcohols containing inert substituents such as halogen atoms, sulfoxide groups, sulfone groups, carbonyl or carboxylic acid ester groups may also be used. Alcohols containing ether bridges are also suitable for the practice of the present invention. Examples of appropriate alcohols are: methanol, ethanol, n-propanol, isopropanol, n-butanol, n-pentanol, n-hexanol, cyclohexanol, benzyl alcohol, chloroethanol, ethylene glycol, diethylene glycol, propylene glycol, dipropylene glycol, glycerol, hexane triol and trimethylol propane.

If an alcohol having a hydroxyl functionality greater than one is used, a monobasic amine should be used as the starting component in the process of the present invention. Conversely, if higher functionality amines are used, a monofunctional hydroxyl compound should be used as a reactant. Monohydric aliphatic alcohols containing from 1 to 6 carbon atoms are the preferred hydroxyl reactants in the process of the present invention.

Phenols suitable for the practice of the present invention are those having a molecular weight in the range from 94 to 600, preferably in the range from 94 to 300. Examples of such phenols include: phenol, α-naphthol, β-naphthol, anthranol, phenanthrol, hydroxybenzofurans and hydroxy quinolines. Polyhydric phenols such as dihydroxybenzenes, dihydroxy naphthalenes, 4,4'-dihydroxy diphenylmethane, bisphenol A, pyrogallol and phloroglucinol may also be used. Any of the above-mentioned phenols containing inert substituents such as halogen atoms, sulfoxide groups, sulfone groups, carboxyl or carboxylic acid ester groups, nitro groups, alkyl groups, aryl groups, alkoxy groups and aroxy groups are also suitable. Particularly preferred phenols are phenol, the isomeric chlorophenols, bisphenol A, 2-isopropoxy phenol and 7-hydroxy-2,2-dimethyl-2,3-dihydrobenzofuran.

In practicing the process of the present invention, the organic compounds containing hydroxyl groups should generally be used in quantities such that from 1 to 200 mols and preferably from 1 to 50 mols of hydroxyl groups are present for each mol of primary amino group present in the reaction mixture. Since hydroxyl compounds which are liquid under the reaction conditions are generally used as reactants, when used in excess amounts these compounds may serve as the reaction medium (solvent) for the process according to the invention.

The carbon monoxide is generally used in a quantity such that between 1 and 30 mols of carbon monoxide are present for each mol of urethane to be produced, i.e. from 1 to 30 mols of carbon monoxide are generally used for each mol of primary amino groups present in the reaction mixture.

Molecular oxygen in pure form or in the form of a mixture with an inert gas (e.g. nitrogen or carbon dioxide) such as air, may be used as the oxidizing agent in the process of the present invention. In the presence of molecular oxygen, the oxycarbonylation reaction takes place in accordance with the following general equation:

$$R\ NH_2 + \tfrac{1}{2}O_2 + CO + R'OH \rightarrow R\ NHCO_2R' + H_2O.$$

It is readily seen from this equation that 1 mol of carbon monoxide and ½ mol of oxygen are required for each urethane group formed. In general, molecular oxygen may be used in an amount ranging from a substantially stoichiometric quantity to a 5-fold excess (based on the amino groups to be reacted). However, where alcohols sensitive to oxidizing agents are used as reactants, it may be advisable to use the oxidizing agent (particularly oxygen) in a sub-stoichiometric quantity (based on the amino groups to be reacted), i.e. in a quantity which corresponds to between 60 and 100% of the equivalent quantity required in accordance with the above equation. Use of less than stoichiometric quantities when oxidation-sensitive alcohols are used is advantageous because the decrease in yield of urethane attributable to undesirable oxidation reactions may be greater than the decrease which occurs when substoichiometric quantities of oxidizing agent are used. In addition, where a sub-stoichiometric quantity of oxidizing agent, particularly oxygen, is used the reaction mixture will contain readily recoverable starting amine which may be re-used in a subsequent reaction. However, when excess oxidizing agent is present in a reaction mixture containing such an oxidation-sensitive alcohol, the alcohol will be destroyed by undesirable oxidation reactions and cannot be recovered.

In addition to oxygen, other suitable oxidizing agents include any oxidizing, inorganic, largely ionic compounds (particularly salt-like compounds) of metals in relatively high valency stages which metals may have several valency stages. The nature of the anions in these compounds is not important. Appropriate anionic groups are chloride, bromide, hydroxide, sulfate, hydrogen sulfate, phosphate, nitrate and carbonate anions. These anions may be present singly or in combination with one another or in combination with oxyanions (i.e. anions in which oxygen is present). Similarly, organic counterions, for example carboxylate, sulfonate, phosphonate, alcoholate and phenolate ions may also be present as anions.

The largely ionic compounds of metals having atomic numbers 22 to 29, 42, 47, 50, 51, 58, 74, 80 to 83 and 92 in high positive valency stages are particularly preferred inorganic oxidizing agents. Where inorganic oxidizing agents of this type are used, it is desirable to select one which has a minimal corrosive effect and a certain solubility in the reaction mixture. Both the corrosion behavior and the solubility of the inorganic oxidizing agent may be favorably influenced by formation of a complex of the oxidizing agent with the mixture of starting materials containing amino groups and/or with the organic constituents of the catalyst system.

Where a largely ionic inorganic oxidizing agent is used, the oxycarbonylation reaction takes place in accordance with the following general equation:

$$RNH_2 + \tfrac{2}{a}M^{n+} + CO + R'OH \longrightarrow$$

$$RNHCO_2R' + \frac{2}{a} M^{(n-a)+} + 2H^+ .$$

In this equation, $M^{n+}$ is a metal having an "n+" oxidation state. In the oxycarbonylation reaction, this metal takes up "a" electrons. Where these largely ionic inorganic oxidizing agents are the only oxidizing agents used, they are generally employed in quantities such that from 2/a to 10/a gram equivalents (preferably from 2/a to 3/a gram equivalents) of oxidizing inorganic compound are available in the reaction mixture for each mol of primary amino groups.

Other oxidizing agents suitable to the practice of the present invention are quinoid organic compounds which, by virtue of their oxidation potential, are capable of oxidizing the amine under the reaction conditions. Quinoid organic compounds of this type include quinones, such as o-benzoquinone, p-benzoquinone, naphthoquinones, and anthraquinones in substituted or unsubstituted form. Suitable substituents are electron-attracting groups which increase the oxidation potential of the quinoid compound, such as carboxylic acid, sulfonic acid, cyano groups and halogen substituents either individually or in combination with one another. Where these quinoid oxidizing agents are exclusively used, they should generally be employed in quantities such that at least one mol of quinoid structural units (i.e. where p-benzoquinone is used, at least one mol of this quinone) is available for every mol of primary amino groups. In addition to these quinones, the quinoid compounds described hereinafter as suitable co-catalysts may also be used as the quinoid compounds.

Where quinoid oxidizing agents are used in the oxycarbonylation of the primary amines in accordance with the present invention, the reaction takes place as exemplyfied with the following equation:

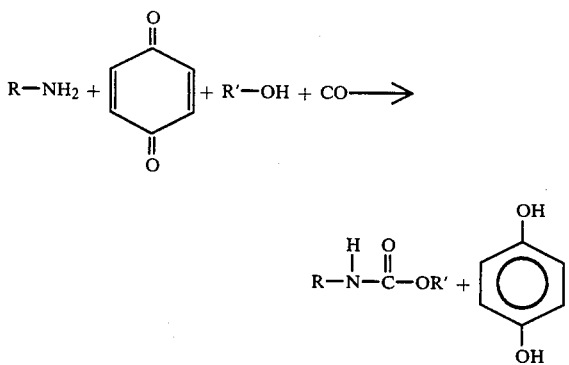

Where these quinoid oxidizing agents are used in the process of the present invention, they should preferably be employed in quantities ranging from the stoichiometric quantity corresponding to the above reaction equation to approximately 5 times the stoichiometric metric quantity and most preferably between 1 and 1.5 times the stoichiometric quantity. Where several of the above-described oxidizing agents are simultaneously used, the quantity in which each is used may of course be reduced accordingly. Where the ionic and/or quinoid oxidizing agents described above are exclusively used, any oxidation-sensitive alcohols present are less likely to be destroyed by oxidation than where molecular oxygen is used. Accordingly, the ionic and/or quinoid oxidizing agents should not generally be used in substoichiometric quantities because this would only result in decreased yield.

The process of the present invention is carried out in the presence of a catalyst system. Such a catalyst system contains (i) at least one noble metal and/or at least one noble metal compound of the Eighth Secondary Group of the Periodic System of Elements and (ii) at least one oxidizing quinoid compound and/or at least one compound which is capable of being converted into an oxidizing quinoid compound under the reaction conditions.

Catalyst component (i) may be either a free noble metal of the Eighth Secondary Group of the Periodic System or a compound of one of these metals. These noble metals are particularly advantageous when used in the form of compounds soluble in the reaction mixture, such as chlorides, bromides, iodides, chlorocomplexes, bromocomplexes, iodocomplexes, acetates, acetyl acetonates and other soluble noble metal compounds. Preferred noble metals are palladium, ruthenium and rhodium. It is particularly preferred to use palladium, particularly in the form of soluble palladium chloride or palladium acetate.

Preferred concentrations for the catalyst component (i) are generally in the range from 3 to 1000 ppm and most preferably in the range from 5 to 100 ppm, expressed as noble metal and based on the reaction mixture as a whole, including any solvent used. Although higher concentrations of noble metal may be used, such excess is uneconomical and does not further increase the yield of urethane.

Catalyst component (ii) is an oxidizing quinoid compound and/or a compound which is capable of being converted into an oxidizing quinoid compound under the reaction conditions. Quinoid compounds are compounds of the type described for example in "The Chemistry of the Quinoid Compounds", Part I and II (London, Wiley 1974, Editor: Patai) and frequently manufactured as dyes or dye precursors. In principle, catalyst component (ii) may be any quinoid compound of the type capable of oxidizing the noble metal present in catalyst component (i) from the zero oxidation state to a positive oxidation state under the reaction conditions. Those quinoids which are capable of converting palladium, from the oxidation stage zero to the oxidation stage +2 are particularly preferred.

In addition to the above-described quinoid compounds, compounds capable of being converted into such quinoid compounds, i.e. compounds which may be converted into a quinoid compound by an oxidation reaction (e.g. by the oxidizing agent used in the process of the present invention) by solvolysis or by an elimination reaction, may also be used as catalyst component (ii).

Suitable quinoid catalyst components (ii) are ortho- and para-quinones, polynuclear quinones and heterocyclic quinones in substituted and unsubstituted form and also their imino, N-alkyl- or N-aryl-imino derivatives. Specific examples of such compounds are: o-tetrachlorobenzoquinone, p-tetrachlorobenzoquinone, 2,5-dichloro-3,6-dihydroxy-p-benzoquinone, 2-chlorophenyl-1,4-benzoquinone, 2,3-dichloronaphthoquinone, anthraquinone, 1-chloroanthraquinone, 7-chloro-4-hydroxy-1,10-anthraquinone, 1-nitroanthraquinone-2-carboxylic acid, 1,5-dichloroanthraquinone, 1,8-dichloroanthraquinone, 2,6-dichloroanthraquinone, 1,4-dihydroxy anthraquinone, acenaphthylene dione, 5,7- dichloro-1H-indol-2,3-dione, indigo or 1,4-dihydro-2,3-quinoxaline dione.

Polymeric quinoid compounds of the type described for example by H. G. Cassidy and K. A. Kun in "Oxidation-Reduction Polymers" (Polymer Reviews Vol. 11, Interscience Publ. New York 1965), are also suitable for use as catalyst component (ii).

Preferred quinoid compounds are those substituted by one or more electron-attracting substituents, such as chlorine, bromine, cyano, nitro, carboxylic acid or sulfonic acid groups. Such substituents increase the oxidation potential of the quinoid compound. Quinoid compounds which are particularly preferred as catalyst component (ii) are o-tetrachlorobenzoquinone, p-tetrachlorobenzoquinone, 2,5-dichloro-3,6-dihydroxy-p-benzoquinone, 2,3-dichloronaphthoquinone, 7-chloro-4-hydroxy-1,10-anthraquinone, 1,5-dichloroanthraquinone and 1,8-dichloroanthraquinone.

Compounds which are readily converted to quinoid compounds suitable for use as catalyst component (ii) are, for example, ketals of the corresponding quinoid and also hydrogenated forms of those components, particularly the corresponding hydroquinones. Aromatic amines and polynuclear aromatic compounds which are substituted by sulfonic acid, carboxylic acid, nitro or cyano groups or which already contain an oxy group in the ring system may be converted into quinoid catalyst component (ii) under the reaction conditions (e.g. by molecular oxygen). Compounds which are readily converted to a quinoid which may be used as catalyst component (ii) in the present invention are the hydroquinones and ketals of the above-mentioned quinones, 4-amino-2-(phenyl-amino)-benzene sulfonic acid, 5-amino-2-((4-chlorophenyl)-amino)-benzene sulfonic acid, 4,4'-diamino-(1,1'-biphenyl)-3,3'-disulfonic acid, 2-aminobenzene sulfonic acid and benzanthrone-3-carbonitrile.

The catalyst component (ii) should generally be added to the reaction system in a concentration from 0.1 wt. % to 5 wt. % and preferably in concentrations of from 0.5 to 3 wt. % (based on the total quantity of reaction mixture including any solvent used).

The quinoid compounds are capable of performing the dual function of oxidizing agent and catalyst component (ii). When used in this dual capacity, it is necessary to use larger quantities of the quinoid compound than specified above for quinoids used only as an oxidizing agent.

The catalyst component of the present invention may optionally contain certain metal compounds (iii) and/or tertiary amines (iv) as further components.

The optional catalyst component (iii) may be a magnesium compound, particularly an inorganic or an organic salt of magnesium, or a compound of an element of the Third to Fifth Main Group and/or First to Eighth Secondary Group of the Periodic System of Elements which is capable of undergoing a redox reaction under the reaction conditions. Compounds of metals with the atomic numbers 12, 22 to 29, 41, 47, 58 and 92 which are at least partly soluble in the reaction mixture are preferably used as the optional catalyst component (iii). The most preferred catalyst components (iii) are the acetates, nitrates and chlorides of chromium, manganese, cobalt, copper, cerium or magnesium, which may be in the form of the hydrates or amine complexes of these metal salts. In conjunction with activating chlorides, (e.g. ammonium chlorides) it is also possible to use the oxides of these metals as catalyst component (iii). If catalyst component (iii) is used, it should generally be employed in an amount which is from one to ten times the required molar quantity (based on catalyst component (i)). In general, this means that catalyst component (iii) may be used in quantities of up to 0.1 wt. % (based on the total weight of the reaction mixture including any solvent used).

The optional catalyst component (iv) may be any tertiary amine which, in the catalyst system, performs the function of a complexing agent for the oxidized form of catalyst component (i). It is particularly advantageous to use a tertiary amine which is also capable of forming a complex with component (iii) in case the complexing effect of the starting compounds present in the reaction mixture is inadequate for this purpose. In principle, any tertiary amines, i.e. tertiary amines of the type containing aliphatically, cycloaliphatically, araliphatically and/or aromatically bound tertiary amino groups or tertiary amino groups forming part of a heterocyclic ring may be used in the practice of the present invention. Suitable tertiary amines are, for example, triethyl amine, diisopropyl methyl amine, cyclohexyl diethyl amine, triphenyl amine, N,N-diethyl aniline, N-phenyl piperidine, pyridine, quinoline, 1,4-diaza-(2,2,2)-bicyclooctane and pyrimidine. Preferred tertiary amines (iv) are triethyl amine, N,N-diethyl aniline and pyridine. The above-mentioned tertiary amines may also be used in the form of metal salt complexes of catalyst component (i) and optionally (iii). If catalyst component (i) and/or optionally (iii) is used in the oxide form, it is advantageous to use the tertiary amines in the form of hydrochlorides for the purpose of activating this (these) component(s). The optional catalyst component (iv) should be used in quantities of up to 10 wt. %, preferably from 0.5 to 6 wt. % (based on the total quantity of reaction mixture including any solvent used). However, catalyst component (iv) may be used in larger quantities.

The process of the present invention may be carried out in the presence or absence of a solvent. In general, the reactant organic hydroxyl compound preferably used in excess serves as solvent. However, it is also possible to use inert solvents which may make up as much as 80 wt. % of the total reaction mixture. The quantity of solvent used, whether the hydroxyl compound used in excess or an inert solvent, should be such that the heat of reaction of the exothermic urethane-forming reaction may be dissipated without any unacceptable increase in temperature. In general, therefore, the process according to the invention is carried out using a concentration of amino compounds of from 5 to 50 wt. % and preferably from 5 to 20 wt. % (based on the total reaction mixture including the solvent).

Suitable solvents are solvents which are inert both to the reaction components and to the catalyst system. Such solvents include aromatic, cycloaliphatic and aliphatic hydrocarbons which may optionally be halogen-substituted, such as benzene, toluene, xylene, chlorobenzene, dichlorobenzene, trichlorobenzene, chloronaphthalene, cyclohexane, methyl cyclohexane, chlorocyclohexane, methylene chloride, carbon tetrachloride, tetrachloroethane, trichlorotrifluoroethane and similar compounds as well as tertiary amines of the type described as catalyst component (iv).

The reaction temperature should generally be in the range from 100 to about 300° C., preferably in the range from 100 to 250° C. and most preferably in the range from 140 to 220° C. The pressure should be such that the presence of a liquid phase is guaranteed. This pressure is generally in the range from 5 to 500 bars and preferably in the range from 30 to 300 bars.

Depending upon the primary amine and hydroxy compound used, the reaction time required for a quantitative reaction ranges from a few minutes to several hours.

The process according to the invention may be carried out continuously or in batches. It is advantageous to use a solvent in which the end product (urethane) is highly soluble. After the reaction medium has been relieved of pressure and cooled to between 50° and 80° C., catalyst components (i), (ii), (iii) and, in complexed form (iv) (if it has been used) are substantially or completely precipitated in numerous solvents. In some cases, it is advantageous to concentrate the reaction mixture to between 70 and 50% of its original volume to precipitate the catalyst mixture. The catalyst mixture may then be separated off from the urethane-containing solution by filtration or centrifugation. The thus-recovered catalyst components (i), (ii), (iii) and, optionally, (iv) may be recycled in most cases even though they may be chemically modified. The urethane may be separated from the filtrate by techniques known to those in the art such as evaporating the solvent. The product urethane may be purified for example by vacuum distillation or by crystallization. The product urethane may be similarly treated where salt-like inorganic oxidizing agents or quinone-like oxidizing agents are used. The oxidizing agent obtained in reduced form after the reaction has been completed contains substantial amounts of catalyst components (i), (ii) and (iii). This oxidizing agent may be reoxidized and recycled along with these catalyst components to the reaction chamber.

The end products (urethanes) of the present invention are suitable for use as pesticides or as intermediate products in the production of pesticides. However, these urethanes are of primary interest as starting materials for producing the isocyanates on which they are based. Production of such isocyanates is carried out in known manner by thermal dissociation of the urethanes of the present invention.

The process according to the invention is illustrated by the following Examples although this invention is in no way limited to the conditions disclosed in these Examples. The urethane yields are based in each case on the amine used and are given in terms of mol percent.

EXAMPLES

EXAMPLE 1

(Comparison Example: No catalyst component (ii))

474 g of a mixture having the following composition were introduced into an enamelled 1.3-liter fine-steel autoclave: 42 ppm of palladium acetate, 211 ppm of copper (II) acetate monohydrate, 91.4 wt. % ethanol and 8.6 wt. % aniline. 100 bars of carbon monoxide and 25 bars of air were then introduced into the autoclave at room temperature. The contents of the autoclave were then heated with stirring to 180° C. and left to react for 1 hour at that temperature. After cooling to room temperature, the autoclave was vented and a second similar reaction phase was carried out with a fresh CO/air mixture. A total of approximately 1.4 oxidation equivalents (based on aniline) were introduced in the form of atmospheric oxygen. Analysis of the liquid reaction mixture by gas chromatography showed that the yield of phenyl urethane was 4.5 mol %, based on the aniline used.

EXAMPLES 2 TO 9

These Examples demonstrate the catalytic activity of catalyst component (ii). In Examples 2 to 6, catalyst component (ii) was a quinoid compound and in Examples 7 to 9, it was the preliminary state of a quinoid compound. The procedure was the same as that described in Example 1, with the exception that 483 g of a mixture of the following composition was used: 41 ppm of palladium acetate, 207 ppm of copper (II) acetate monohydrate, 1.8 wt. % catalyst component (ii), 89.8 wt. % ethanol and 8.4 wt. % aniline. The results are set out in Table 1.

TABLE 1

| Example No. | Catalyst component (ii) | Yield of phenyl urethane in mol % |
|---|---|---|
| 2 | ortho-tetrachlorobenzoquinone | 46.0 |
| 3 | para-tetrachlorobenzoquinone | 64.0 |
| 4 | 2,5-dichloro-3,6-dihydroxy-para-benzoquinone | 47.5 |
| 5 | 2,3-dichloronaphthoquinone | 52.5 |
| 6 | 1,5-dichloroanthraquinone | 40.9 |
| 7 | benzanthrone-3-carbonitrile | 27.1 |
| 8 | 5-amino-2-(phenylamino)-benzene sulfonic acid | 29.0 |
| 9 | 4,4'-diamino-(1,1'-biphenyl)-3,3'-disulfonic acid | 32.0 |

EXAMPLE 10

The procedure was the same as that described in Example 1 with the exception that 487 g of a mixture of the following composition were used: 41 ppm of palladium acetate, 206 ppm of copper (II) acetate monohydrate, 1.7 wt. % p-tetrachlorobenzoquinone, 0.8 wt. % N,N-diethylaniline, 89.0 wt. % ethanol and 8.4 wt. % aniline. Yield of phenyl urethane: 72.6 mol %.

EXAMPLE 11

The procedure was the same as that described in Example 1 with the exception that 483 g of a mixture of the following composition were used: 41 ppm of palladium acetate, 207 ppm of copper (II) acetate monohydrate, 1.8 wt. % p-tetrachlorobenzoquinone, 48.3 wt. % ethanol, 8.4 wt. % aniline and 41.5 wt. % ortho-dichlorobenzene. Yield of phenyl urethane: 71.8 mol %.

EXAMPLES 12 TO 17

These Examples demonstrate the catalytic activity of various noble metals which may be used as catalyst component (i). The procedure was the same as that described in Example 1, except that 483 g of a reaction mixture having the following composition were used: 104 ppm of catalyst component (i), 207 ppm of copper (II) acetate monohydrate, 1.8 wt. % p-tetrachlorobenzoquinone, 89.8 wt. % ethanol and 8.4 wt. % aniline. The results obtained are set out in Table 2. Example 12 is a Comparison Example in which no catalyst component (i) was used.

TABLE 2

| Example No. | Catalyst component (i) | Yield of phenyl urethane in mole % |
|---|---|---|
| 12 | — | 1.0 |
| 13 | RuCl$_3$ | 55.6 |
| 14 | RhCl$_3$ | 38.9 |
| 15 | PdCl$_2$ | 57.2 |

TABLE 2-continued

| Example No. | Catalyst component (i) | Yield of phenyl urethane in mole % |
|---|---|---|
| 16 | IrCl$_3$ | 5.5 |
| 17 | PtCl$_2$ | 4.4 |

EXAMPLE 18

This Example demonstrates that catalyst components (i) and (ii) catalyze the urethane-forming reaction even in the absence of catalyst components (iii) and (iv). The procedure was the same as that described in Example 1, except that 482 g of a reaction mixture of the following composition were used: 44 ppm of palladium chloride, 1.8 wt. % p-tetrachlorobenzoquinone, 89.8 wt. % ethanol and 8.4 wt. % aniline. Yield of phenyl urethane: 54.6 mol %.

EXAMPLES 19 TO 23

The procedure was the same as that described in Example 1, except that a 0.7 liter fine-steel autoclave filled with 223 g of reaction mixture of the following composition were used: 22 ppm of palladium chloride, 1.8 wt. % p-tetrachlorobenzoquinone, 90 ppm of catalyst component (iii), 89.8 wt. % ethanol and 8.4 wt. % aniline. The results are shown in Table 3.

TABLE 3

| Example No. | Catalyst component (iii) | Yield of polyurethane in mol % |
|---|---|---|
| 19 | Cr(NO$_3$)$_3$.9 H$_2$O | 59.4 |
| 20 | Mn(OAc)$_2$.H$_2$O | 60.2 |
| 21 | Co(OAc)$_2$.H$_2$O | 65.3 |
| 22 | Cu(OAc)$_2$.H$_2$O | 62.1 |
| 23 | Mg(NO$_3$)$_2$.6 H$_2$O | 60.7 |

EXAMPLE 24

This Example demonstrates the catalytic activity of a recycled catalyst. The solid precipitated was filtered off from the product mixture of Example 3, and dried at 50° C. 111 g of a mixture of the following composition were then reacted under the same conditions as described in Example 3 in a 0.3 liter fine-steel autoclave using 1.8 wt. % recovered catalyst mixture, 8.4 wt. % aniline and 89.8 wt. % ethanol. Yield of phenyl urethane: 62.4 mol %.

EXAMPLES 25 TO 29

111.4 g of a mixture of the following composition were introduced into a 0.3 liter fine-steel autoclave: 90 ppm of palladium acetate, 450 ppm of copper acetate monohydrate, 1.8 wt. % tetrachloro-p-benzoquinone, 8.4 wt. % aniline and 89.8 wt. % hydroxy component (see Table 4). 100 bars of carbon monoxide and 25 bars of air were introduced at room temperature. Accordingly, approximately 0.7 oxidation equivalents based on aniline were introduced in the form of atmospheric oxygen. The contents of the autoclave were left to react for 1 hour at 180° C. After cooling, the urethane yields given in Table 4 were obtained according to analysis by gas chromatography.

TABLE 4

| Hydroxy component | Yield of N—phenyl urethane in mol % |
|---|---|
| ethanol | 58 |
| 1-propanol | 64 |
| 2-propanol | 62 |
| cyclohexanol | 34 |
| benzyl alcohol | 20 |

EXAMPLE 30

129.4 g of a mixture of the following composition were introduced into a 0.3 liter fine-steel autoclave: 31 ppm of palladium acetate, 232 ppm of copper acetate monohydrate, 1.5 wt. % tetrachloro-p-benzoquinone, 5.4 wt. % pyridine, 8.5 wt. % (0.1 mol) p-benzoquinone, 7.3 wt. % (0.1 mol) aniline and 77.3 wt. % ethanol. 120 bars of CO were introduced at room temperature. After a reaction time of 2 hours at 180° C., the yield of phenyl urethane amounted to 34 mol % according to analysis by gas chromatography.

EXAMPLE 31

The procedure was the same as that described in Example 30 with the exception that 127.8 g of a starting mixture of the following composition were used: 31 ppm of palladium acetate, 1.6 wt. % tetrachloro-p-benzoquinone, 5.5 wt. % (0.05 mol) copper (II) chloride, 3.4 wt. % (0.05 mol) copper (II) oxide, 3.9 wt. % pyridine, 7.4 wt. % (0.1 mol) aniline and 78.2 wt. % ethanol. Yield of phenyl urethane: 40 mol %.

EXAMPLE 32

216.7 g of a mixture of the following composition were introduced into a 0.7 liter fine-steel autoclave: 50 ppm of palladium acetate, 250 ppm of copper acetate monohydrate, 2.2 wt. % 2,3-dichloronaphtoquinone, 5.5 wt. % tert.-butyl amine and 92.3 wt. % ethanol. 100 bars of CO and 25 bars of air were introduced at room temperature. Accordingly, approximately 1.2 oxidation equivalents based on tert.-butyl amine were introduced in the form of atmospheric oxygen. The contents of the autoclave were left to react with stirring for 1 hour at 180° C. After cooling, analysis by gas chromatography showed a yield of N-tert.-butyl-O-ethyl urethane of 32 mol %.

What is claimed is:

1. A process for the production of a urethane by reacting a primary amine with carbon monoxide and a compound containing at least one hydroxyl group in the presence of from 60 to 500% of the stoichiometric amount of oxygen necessary to react with the amino groups to be reacted and a catalyst system, said catalyst system comprising:
   (a) palladium, a palladium compound or a mixture thereof; and
   (b) an oxidizing quinoid, a compound capable of being converted to an oxidizing quinoid compound under the reaction conditions, or a mixture thereof in an amount of from 0.1 to 5 wt % (based on total weight of reaction mixture).

2. The process of claim 1 wherein the catalyst system further comprises a compound of an element selected from the Third to Fifth Main Groups and/or First to Eighth Secondary Group of the Periodic System of Elements which compound is capable of undergoing a redox reaction under the reaction conditions.

3. The process of claim 1 wherein the catalyst system further comprises a tertiary amine.

4. The process of claim 1 wherein component (a) of the catalyst system is present in an amount which is from 5 ppm to 100 ppm expressed as noble metal and based on the total weight of the reaction mixture.

5. The process of claim 1 wherein the catalyst system further comprises up to 0.1 wt. % (based on the total weight of the reaction mixture) of a compound of an element selected from the Third to Fifth Main Group and/or First to Eighth Secondary Group of the Periodic System of Elements which compound is capable of undergoing a redox reaction under the reaction conditions.

6. The process of claim 5 wherein the catalyst system further comprises up to 10 wt. % (based on the total weight of the reaction mixture) of a tertiary amine.

7. The process of claim 1 wherein the reaction is carried out at a temperature in the range from 100° to 250° C. and under a pressure of from 5 to 500 bars.

8. The process of claim 1 wherein the reaction is carried out in the presence of up to 80 wt. % (based on the total weight of the reaction mixture) of an inert solvent.

9. The process of claim 1 wherein the product urethane is separated from the catalyst system and any remaining oxidizing agent or reduced oxidizing agent by distillation and/or filtration.

10. The process of claim 9 wherein the separated catalyst system is reused in a subsequent reaction.

11. The process of claim 1 in which the reaction is carried out in the presence from 100 to 500% of the stoichiometric amount of oxygen necessary to react with the amino groups to be reacted.

* * * * *